(12) United States Patent
Schmidt et al.

(10) Patent No.: US 9,700,732 B2
(45) Date of Patent: Jul. 11, 2017

(54) LEADLESS CARDIAC PACEMAKER AND RETRIEVAL DEVICE

(71) Applicant: Cardiac Pacemakers, Inc., St. Paul, MN (US)

(72) Inventors: Brian L. Schmidt, White Bear Lake, MN (US); Dana Sachs, Pine City, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 190 days.

(21) Appl. No.: 14/451,553

(22) Filed: Aug. 5, 2014

(65) Prior Publication Data

US 2015/0051609 A1 Feb. 19, 2015

Related U.S. Application Data

(60) Provisional application No. 61/866,650, filed on Aug. 16, 2013.

(51) Int. Cl.
| | |
|---|---|
| *A61B 19/00* | (2006.01) |
| *A61N 1/375* | (2006.01) |
| *A61N 1/362* | (2006.01) |
| *A61N 1/05* | (2006.01) |

(52) U.S. Cl.
CPC ........... *A61N 1/3756* (2013.01); *A61N 1/362* (2013.01); *A61N 2001/0578* (2013.01)

(58) Field of Classification Search
CPC ............. A61N 1/3756; A61N 1/37205; A61N 2001/0578; A61N 1/362; A61N 1/0573; A61N 1/059; A61N 1/372; A61N 2001/058; A61N 1/057; A61N 1/0587; A61B 5/0215

USPC ............... 606/129; 607/122, 126, 127, 128; 600/373
See application file for complete search history.

(56) References Cited

U.S. PATENT DOCUMENTS

| | | | |
|---|---|---|---|
| 721,869 A | 3/1903 | Dunning | |
| 3,717,151 A | 2/1973 | Collett | |
| 3,754,555 A | 8/1973 | Schmitt | |
| 3,814,104 A | 6/1974 | Irnich et al. | |

(Continued)

FOREIGN PATENT DOCUMENTS

| | | |
|---|---|---|
| CA | 1003904 A1 | 1/1977 |
| DE | 2053919 A1 | 5/1972 |

(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Katherine M Shi
(74) *Attorney, Agent, or Firm* — Seager, Tufte & Wickhem LLP

(57) ABSTRACT

A retrieval device and an associated implantable cardiac pacing device. The retrieval device includes a retrieval catheter and a snare advanceable from the distal end of the retrieval catheter. The snare has a loop configured to be coupled to the docking member to draw the implantable cardiac pacing device into the lumen of the retrieval catheter. The retrieval catheter includes a retention feature in the lumen configured to engage the head portion of the docking member to facilitate retention of the implantable cardiac pacing device in the lumen after drawing the implantable cardiac pacing device into the lumen of the retrieval catheter with the snare.

14 Claims, 24 Drawing Sheets

(56) References Cited

U.S. PATENT DOCUMENTS

| | | |
|---|---|---|
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Fröberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,993,351 B2 | 8/2011 | Worley et al. |
| 8,010,209 B2 | 8/2011 | Jacobson |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |

(56) References Cited

U.S. PATENT DOCUMENTS

| | | |
|---|---|---|
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 2002/0077556 A1 | 6/2002 | Schwartz |
| 2003/0004537 A1 | 1/2003 | Boyle et al. |
| 2004/0176797 A1 | 9/2004 | Opolski |
| 2005/0090890 A1 | 4/2005 | Wu et al. |
| 2005/0267555 A1 | 12/2005 | Marnfeldt et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2009/0082828 A1 | 3/2009 | Ostroff |
| 2009/0281605 A1 | 11/2009 | Marnfeldt et al. |
| 2010/0198288 A1 | 8/2010 | Ostroff |
| 2011/0034939 A1 | 2/2011 | Kveen et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0096672 A1* | 4/2013 | Reich ............... A61F 2/2466 623/2.11 |
| 2013/0103047 A1 | 4/2013 | Steingisser et al. |
| 2013/0103049 A1 | 4/2013 | Bonde |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |

FOREIGN PATENT DOCUMENTS

| | | |
|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2011032157 A1 | 3/2011 |
| WO | 2012058067 A1 | 5/2012 |
| WO | 2012092067 A1 | 7/2012 |
| WO | 2012092074 A1 | 7/2012 |

* cited by examiner

LEADLESS CARDIAC PACEMAKER AND RETRIEVAL DEVICE

CROSS-REFERENCES TO RELATED APPLICATIONS

This application claims the benefit of U.S. Provisional Application No. 61/866,650, filed Aug. 16, 2013, the complete disclosure of which is herein incorporated by reference.

TECHNICAL FIELD

The disclosure is directed to implantable cardiac devices and associated retrieval devices. More particularly, the disclosure is directed to leadless cardiac stimulators or pacemakers having proximal docking members and associated retrieval catheters configured having retrieval features configured to engage the docking members.

BACKGROUND

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber with a fixation mechanism engaging the intracardiac tissue. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition.

Accordingly, there it is desirable to provide alternative structures, assemblies and systems for retrieving leadless cardiac pacemakers from an implantation site in a heart chamber.

SUMMARY

The disclosure is directed to several alternative designs, materials and methods of manufacturing medical device structures and assemblies, and uses thereof.

Accordingly, one illustrative embodiment is an assembly for retrieving an implantable cardiac pacing device. The assembly includes an implantable cardiac pacing device and a retrieval device. The implantable cardiac pacing device has a housing, an electrode positioned proximate a distal end of the housing, and a docking member extending from a proximal end of the housing opposite the distal end. The docking member includes a head portion and a neck portion extending between the housing and the head portion. The retrieval device includes a retrieval catheter having a proximal end, a distal end, and a lumen extending into the retrieval catheter from the distal end, and a snare advanceable from the distal end of the retrieval catheter. The snare has a loop configured to be coupled to the docking member to draw the implantable cardiac pacing device into the lumen of the retrieval catheter. The retrieval catheter includes a retention feature in the lumen configured to engage the head portion of the docking member to facilitate retention of the implantable cardiac pacing device in the lumen after drawing the implantable cardiac pacing device into the lumen of the retrieval catheter with the snare.

Another illustrative embodiment is a method of retrieving an implantable cardiac pacing device from a heart. The implantable cardiac pacing device has a housing having a longitudinal axis, an electrode positioned proximate a distal end of the housing, and a docking member extending from a proximal end of the housing opposite the distal end. The docking member includes a head portion and a neck portion extending between the housing and the head portion. The head portion has a radial dimension from the longitudinal axis and the neck portion having a radial dimension from the longitudinal axis less than the radial dimension of the head portion. The method includes advancing a retrieval device into a heart having the implantable cardiac pacing device implanted therein. The retrieval device includes a retrieval catheter having a lumen therein and a snare advanceable from a distal end of the retrieval catheter. The method further includes encircling the docking member with a loop of the snare and cinching the loop around a portion of the docking member. The snare may then be actuated proximally to pull the implantable cardiac pacing device into the lumen of the retrieval catheter, and the head portion of the docking member may be engaged with a retention feature within the lumen to retain the implantable cardiac pacing device in the lumen after pulling the implantable cardiac pacing device into the lumen of the retrieval catheter with the snare.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
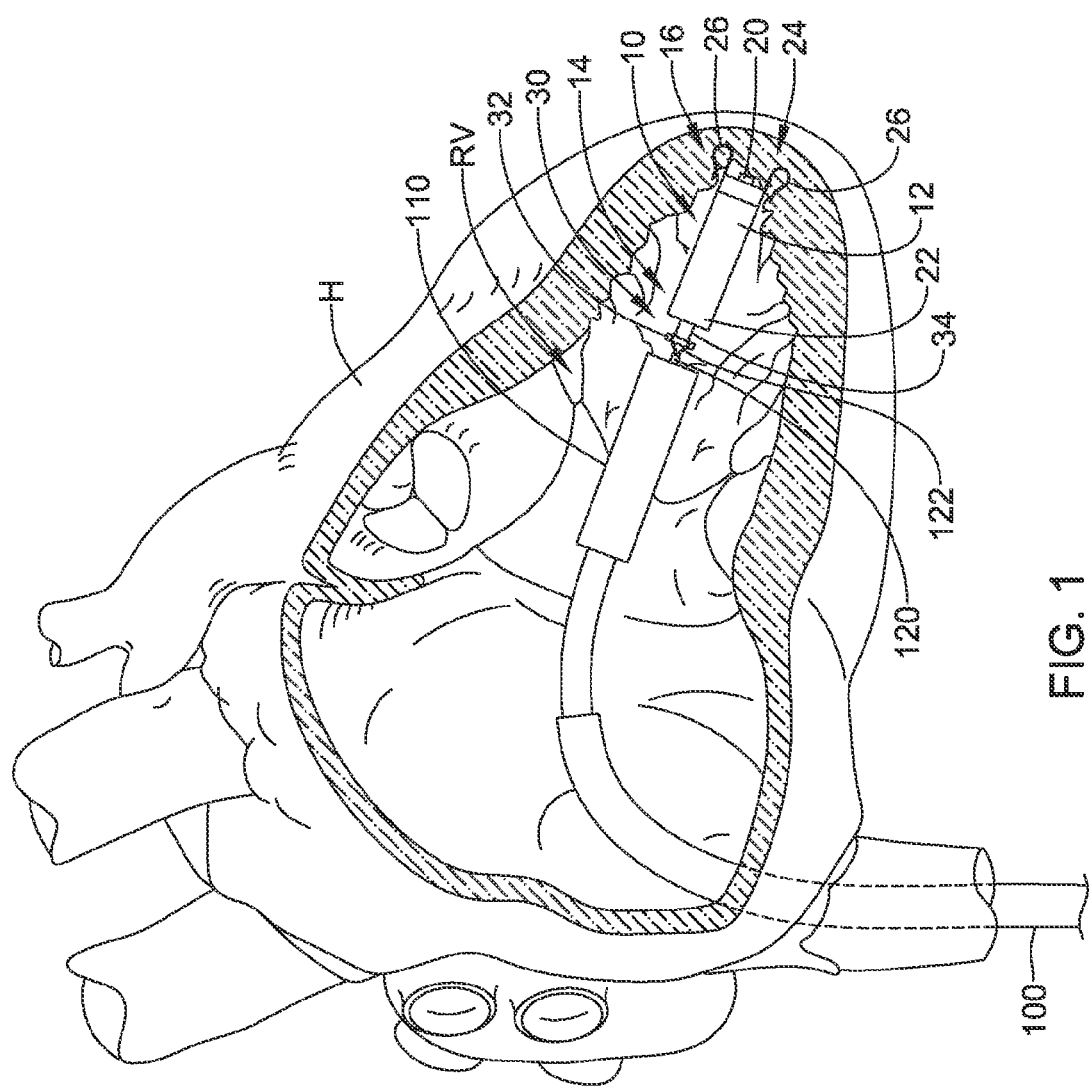
FIG. 1 illustrates an exemplary implantable device implanted in a chamber of a heart and an associated retrieval device retrieving the implantable device during a retrieval procedure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Referring to FIG. 1, an exemplary implantable leadless cardiac pacing device 10 (e.g., a leadless pacemaker) is illustrated implanted in a chamber of a heart H, such as the apex of the right ventricle RV. The implantable device 10 may include a shell or housing 12 having a proximal end 14 and a distal end 16. The implantable device 10 may include a first electrode 20 positioned proximate the distal end 16 of the housing 12 and a second electrode 22 positioned proximate the proximal end 14 of the housing 12. The electrodes 20, 22 may be sensing and/or pacing electrodes to provide electro-therapy and/or sensing capabilities. The first electrode 20 may be configured to be positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Some exemplary embodiments of the docking member 30 are described in further detail herein.

If it is desired to retrieve the implantable device 10 from the heart H, a retrieval device 100 may be advanced into the chamber of the heart H to capture the implantable device 10 and remove the implantable device 10 from the heart H. The retrieval device 100 may be advanced into the right ventricle RV of the heart H, using any desired route. For example, the retrieval device 100 may be through the femoral vein from a femoral access site, through the inferior vena cava, into the right atrium, and through the tricuspid valve into the right ventricle RV. It is noted, however, other pathways may be implemented, if desired.

One exemplary retrieval device 100 is illustrated in FIG. 1. The retrieval device 100 may include a snare 120 advanceable from a lumen of a retrieval catheter 110. In some instances, as shown in FIG. 1, the retrieval catheter 110 may include an elongate shaft having an enlarged distal portion to receive the implantable device 10 therein. The snare 120 may include one or more, or a plurality of loops 122 extending from a distal end of the snare 120 configured to engage the docking member 30 of the implantable device 10. Once the loop(s) 122 of the snare 120 has captured the docking member 30, the snare 120 may be actuated proximally relative to the retrieval catheter 110 to pull the implantable device 10 into the lumen of the retrieval catheter 110. The enlarged size of the head portion 32 relative to the neck portion 34 may permit the loop 122 of the snare 120 to encircle the neck portion 34 below (i.e., distal of) the head portion 32 and retain the loop 122 around the docking member 30 as the snare 120 is pulled proximally. As the implantable device 10 is pulled into the retrieval catheter 110, the fixation mechanism 24 may disengage from the heart tissue to detach the implantable device 10 from the heart wall. For example, the hooks 26 may elongate as the implantable device 10 is drawn proximally into the lumen of the retrieval catheter 110.

As discussed herein, in some instances the retrieval catheter 110 may include an additional or supplemental retention feature configured to engage with the docking member 30 as the implantable device 10 is drawn proximally into the lumen of the retrieval catheter 110. The supplemental retention feature may retain the implantable device 10 in the lumen of the retrieval catheter 110 as the retrieval device 100 and the implantable device 10 are withdrawn from the patient. Thereafter, the retrieval device 100, with the implantable device 10 captured in the lumen of the retrieval catheter 100 with the retention structure and/or snare 120, may be withdrawn from the heart H. Some exemplary embodiments of an additional retention feature are shown in FIGS. 2, 4, 6 and 8, further described herein.

Figure 2:
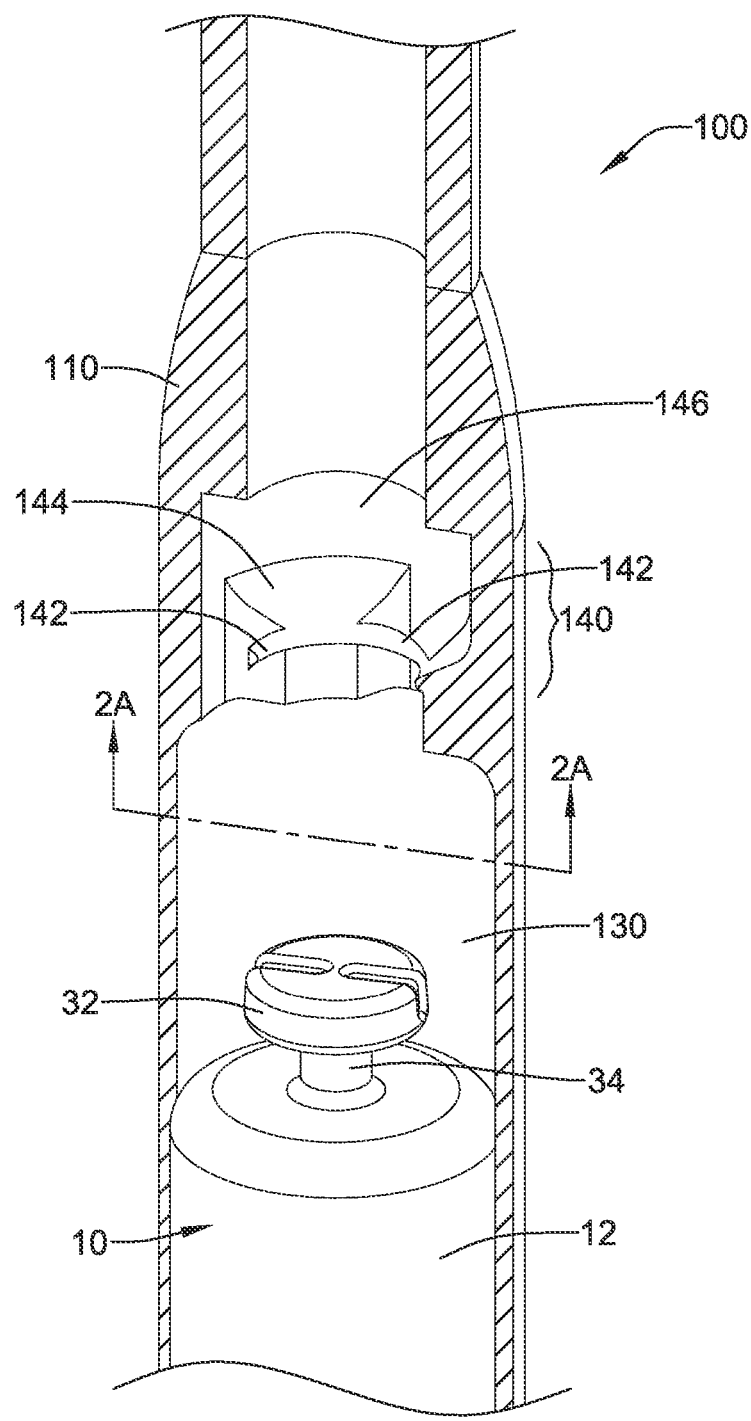
FIG. 2 is a perspective cross-sectional view of an exemplary retention feature of a retrieval device and a perspective view of an associated docking member of an implantable device.

Turning to FIG. 2, an exemplary embodiment of a retention feature 140 located within the retrieval catheter 110 is illustrated. The retention feature 140 may be located within the retrieval catheter 110 proximal of a distal portion of the lumen of the retrieval catheter 110 defining a chamber 130 sized to receive the implantable device 10 therein. The retention feature 140 shown in FIG. 2 may include a circumferential rim 142 projecting into the lumen configured to form a snap fit with the head portion 32 of the docking member 30. For example, the circumferential rim 142 may have an inner diameter less than an outer diameter of the head portion 32 of the docking member 30, such that the circumferential rim 142 is deformed or deflected as the head portion 32 is moved from a location distal of the circumferential rim 142 to a location proximal of the circumferential rim 142. The circumferential rim 142 may be less than the diameter of the chamber 130 within which the housing 12 of the implantable device 10 may be received.

Figure 2A:
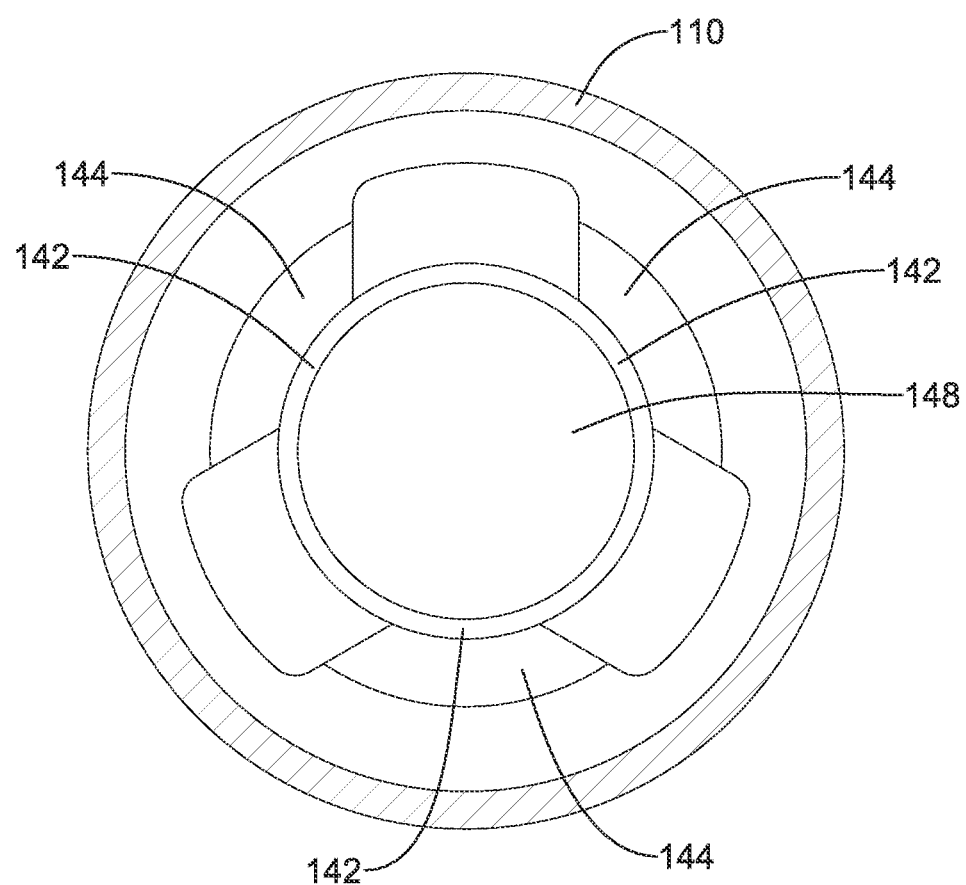
FIG. 2A is a cross-sectional view taken along line 2A-2A of FIG. 2.

As shown in FIGS. 2 and 2A, in some instances the retention feature 140 may include one or more, or a plurality of lands 144 extending radially inward from an inner surface 146 of the retrieval catheter 110. The lands 144 may be symmetrically or asymmetrically spaced apart around the inner surface 146. In some instances, as shown in FIG. 2A, the circumferential rim 142 may be a continuous ring attached to each of the lands 144 and extend continuously between lands 144. In other instances, the circumferential rim 142 may include a plurality of discontinuous segments, with one or more of the discontinuous segments being associated with each of the lands 144. The lands 144 may be sufficiently deflectable to permit the head portion 32 of the docking member 30 to be passed through the central opening 148 defined by the circumferential rim 142 during a retrieval procedure. In other embodiments, the circumferential rim 142, which may be continuous or discontinuous, may extend directly from the inner surface 146.

The circumferential rim 142 and/or the lands 144 may be formed of a flexible material, such as a flexible polymeric material, permitting the circumferential rim 142 and/or lands 144 to deflect or deform when the head portion 32 is pulled through the central opening 148 defined by the circumferential rim 142. In some instances, the circumferential rim 142 and/or the lands 144 may be formed as a unitary structure with the portion of the retrieval catheter 110 defining the chamber 130, or other component of the retrieval catheter 110. However, in other instances, the circumferential rim 142 and/or the lands 144 may be formed as a separate structure.

Figure 3A:
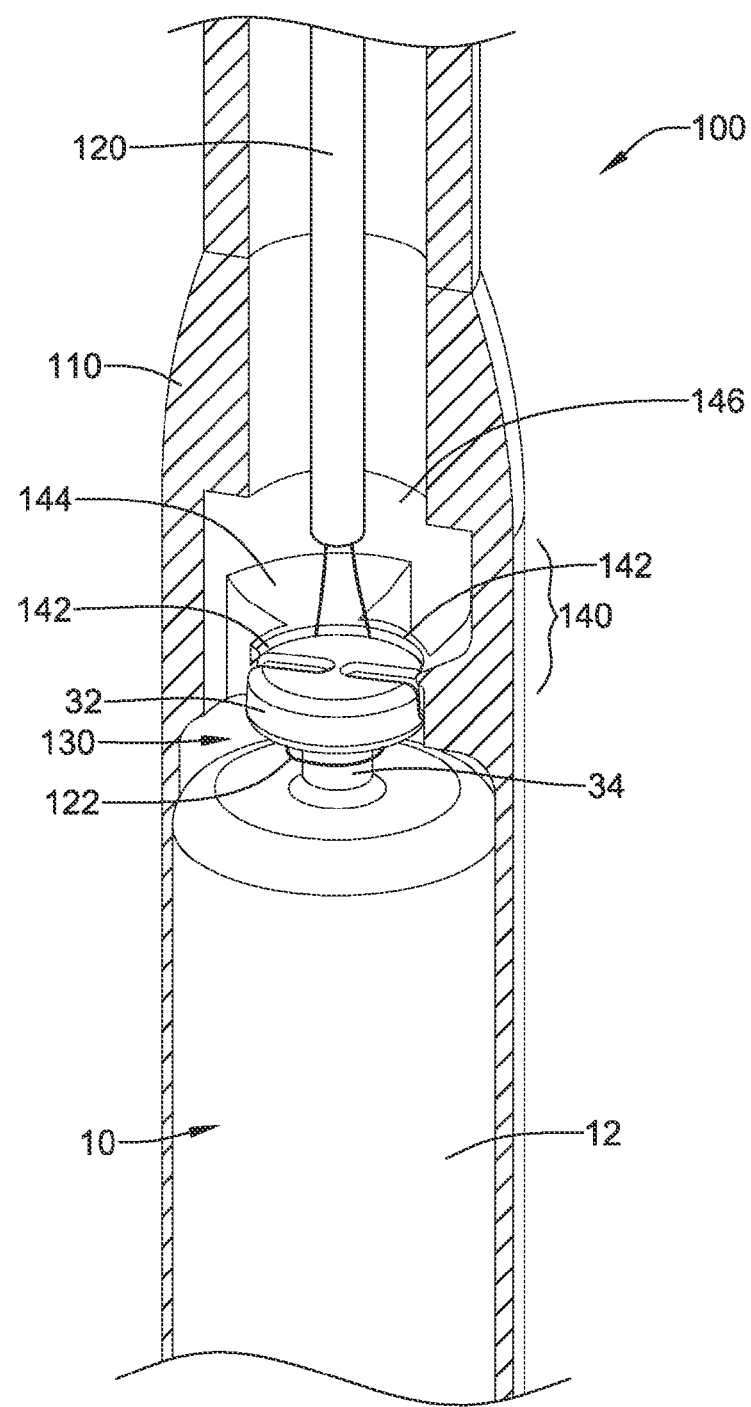
FIGS. 3A and 3B are cross-sectional views illustrating retention of the docking member with the retention feature of FIG. 2 during a retrieval procedure.
Figure 3B:
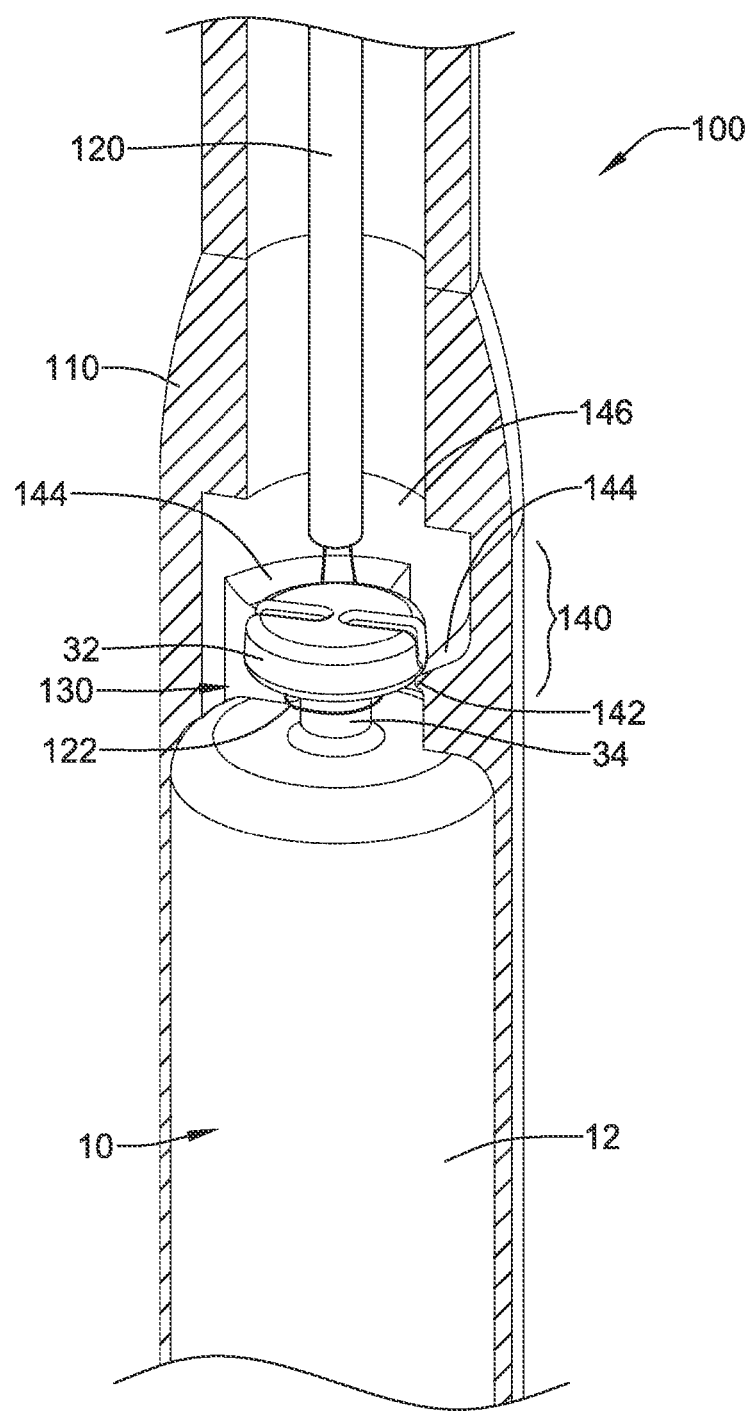

FIGS. 3A and 3B illustrate an exemplary process of engaging the implantable device 10 with the retention feature 140 during a retrieval procedure. During the retrieval procedure the implantable device 10 may be pulled into the chamber 130 of the retrieval catheter 110, such as with the snare 120. For example, with the loop 122 cinched around the docking member 30, the snare 120 may be actuated proximally relative to the retrieval catheter 110 to draw the housing 12 of the implantable device 10 into the chamber 130 at the distal end of the retrieval catheter 110.

The implantable device 10 may be drawn into the chamber 130 with the snare 120 until the docking member 30 is just distal of the circumferential rim 142, as shown in FIG. 3A. The docking member 30 may then be drawn further proximally with the snare 120 by applying a sufficient amount of force to the snare 120 to deflect or deform the circumferential rim 142 a sufficient amount to permit the head portion 32 of the docking member 30 to pass through the opening 148 to a location proximal of the circumferential rim 142, as shown in FIG. 3B, forming a snap fit between the head portion 32 of the docking member 30 and the circumferential rim 142 to lock the implantable device 10 within the chamber 130. Once the head portion 32 of the docking member 30 has passed proximally of the circumferential rim 142, the circumferential rim 142 may revert back to its equilibrium state in which the inner diameter of the circumferential rim 142 is less than the outer diameter of the head portion 32 of the docking member 30. Unless a threshold amount of force is applied to the implantable device 10 to overcome the biasing force of the circumferential rim 142, the circumferential rim 142 will retain the implantable device 10 within the chamber 130. The implantable device 10, retained in the chamber 130 with the retention feature 140 and/or the snare 120 may then be withdrawn from the heart H with the retrieval device 100.

Figure 4:
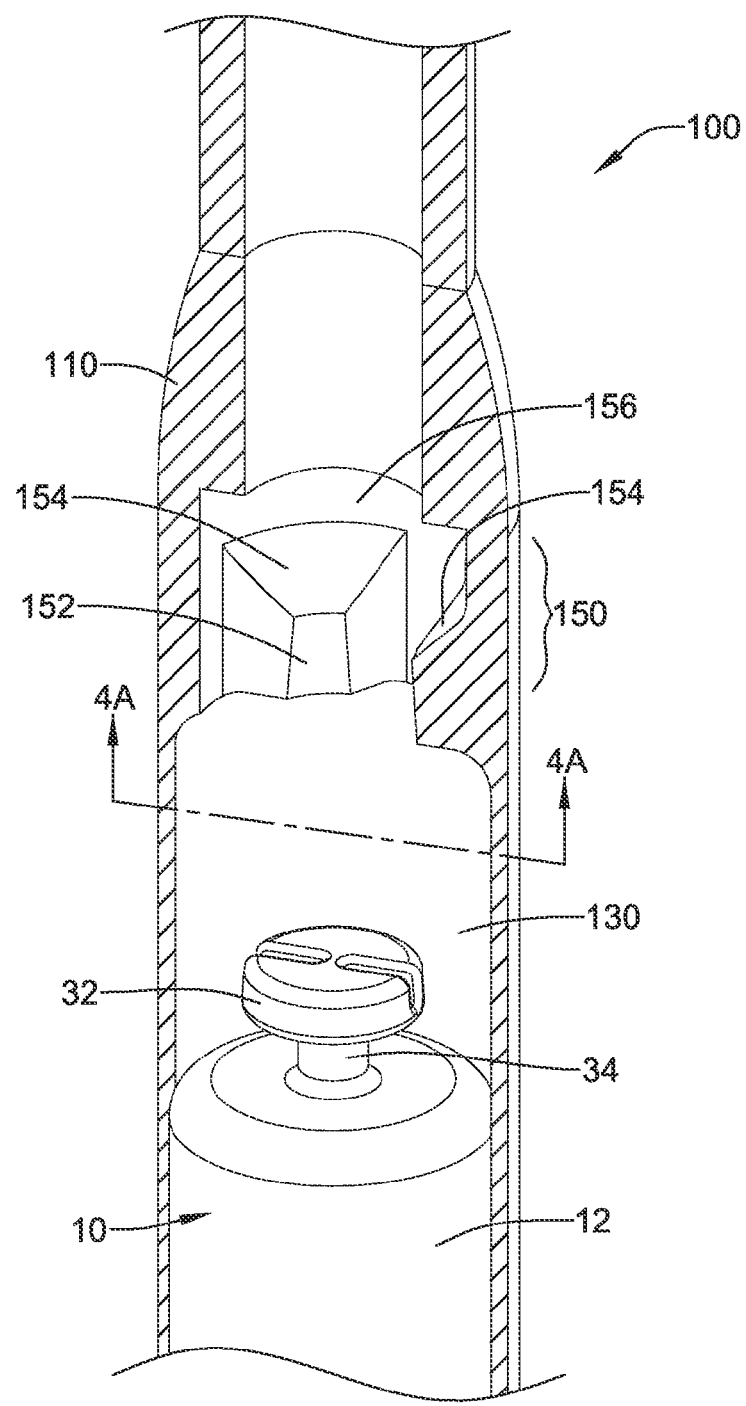
FIG. 4 is a perspective cross-sectional view of another exemplary retention feature of a retrieval device and a perspective view of an associated docking member of an implantable device.

Another exemplary embodiment of a retention feature 150 located within the retrieval catheter 110 is illustrated in FIG. 4. The retention feature 150 may be located within the retrieval catheter 110 proximal of a distal portion of the lumen of the retrieval catheter 110 defining a chamber 130 sized to receive the implantable device 10 therein. The retention feature 150 shown in FIG. 4 may include a tapered interior surface 152 configured to form an interference or frictional fit with the head portion 32 of the docking member 30. For example, the tapered interior surface 152 may taper proximally from a first diameter greater than an outer diameter of the head portion 32 of the docking member 30 to a second diameter less than the outer diameter of the head portion 32 of the docking member 30. In some instances, the proximal portion of the tapered interior surface 152 having the second diameter may have a diameter less than the inner diameter of the chamber 130 within which the housing 12 of the implantable device 10 may be received. In some instances, the tapered surface 152 may be a continuous or discontinuous frustoconical surface.

Figure 4A:
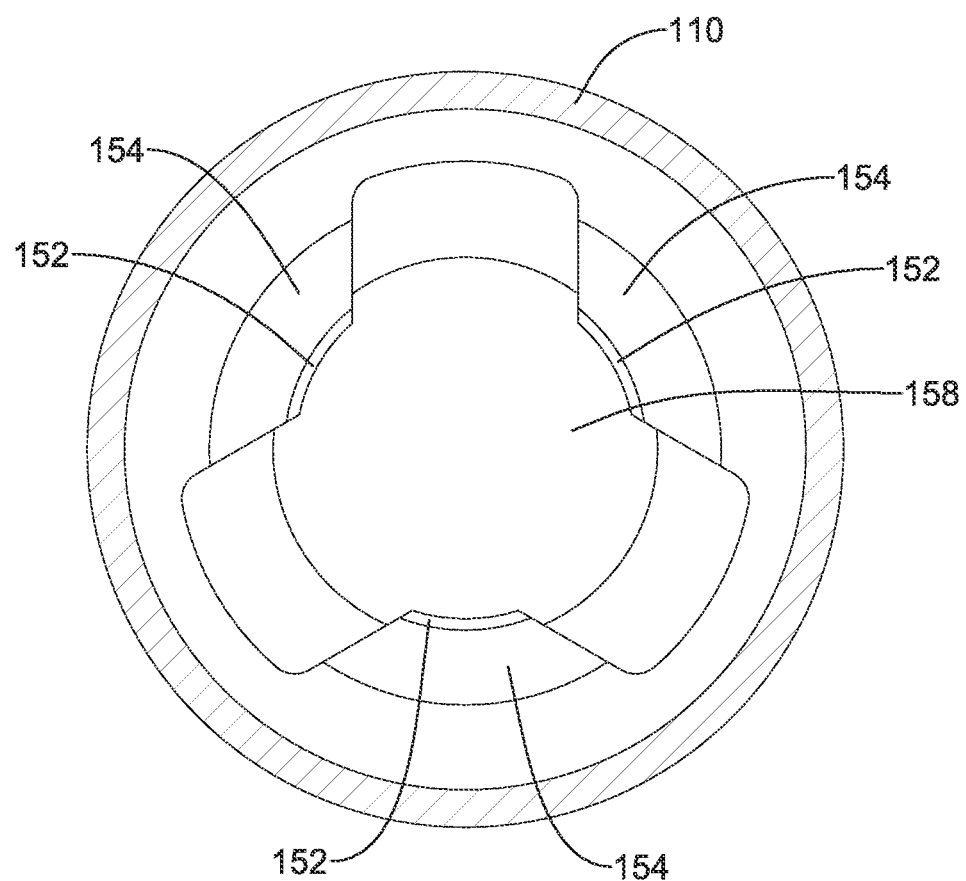
FIG. 4A is a cross-sectional view taken along line 4A-4A of FIG. 4.

As shown in FIGS. 4 and 4A, in some instances the retention feature 150 may include one or more, or a plurality of lands 154 extending radially inward from an inner surface 156 of the retrieval catheter 110. The lands 154 may be symmetrically or asymmetrically spaced apart around the inner surface 156. Accordingly, the tapered surface 152 may be a discontinuous frustoconical surface having a plurality of discontinuous segments, with a discontinuous segment being associated with each of the lands 154.

Figure 5A:
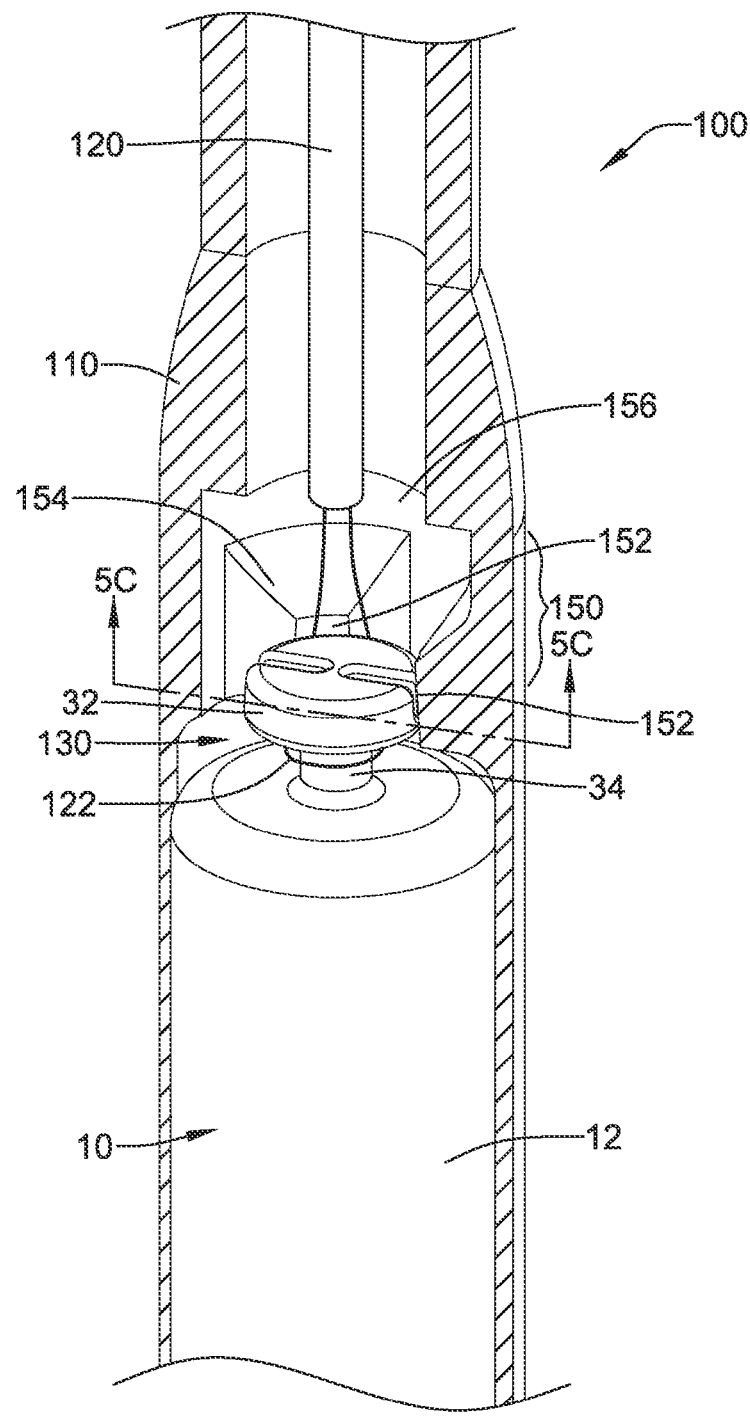
FIGS. 5A and 5B are cross-sectional views illustrating retention of the docking member with the retention feature of FIG. 4 during a retrieval procedure.
Figure 5B:
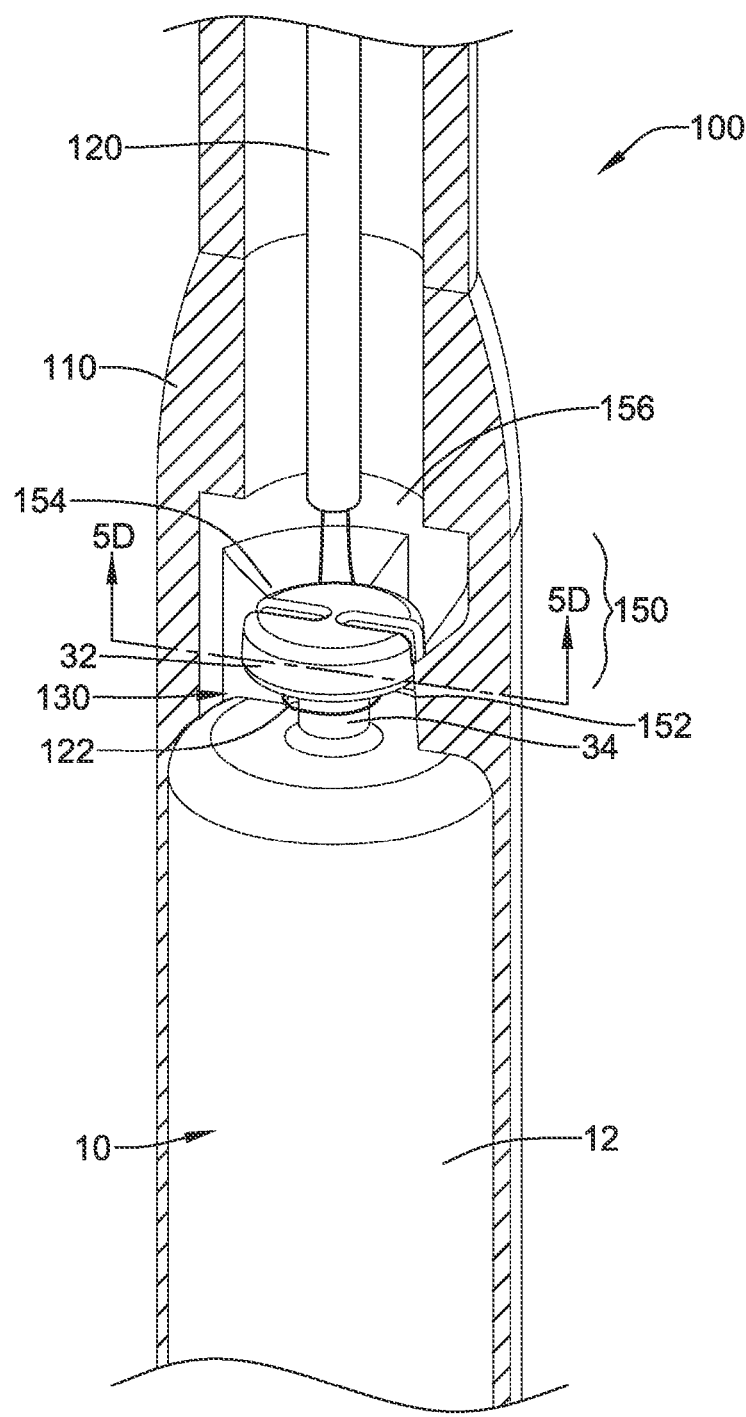

FIGS. 5A and 5B illustrate an exemplary process of engaging the implantable device 10 with the retention feature 150 during a retrieval procedure. During the retrieval procedure the implantable device 10 may be pulled into the chamber 130 of the retrieval catheter 110, such as with the snare 120. For example, with the loop 122 cinched around the docking member 30, the snare 120 may be actuated proximally relative to the retrieval catheter 110 to draw the housing 12 of the implantable device 10 into the chamber 130 at the distal end of the retrieval catheter 110.

Figure 5C:
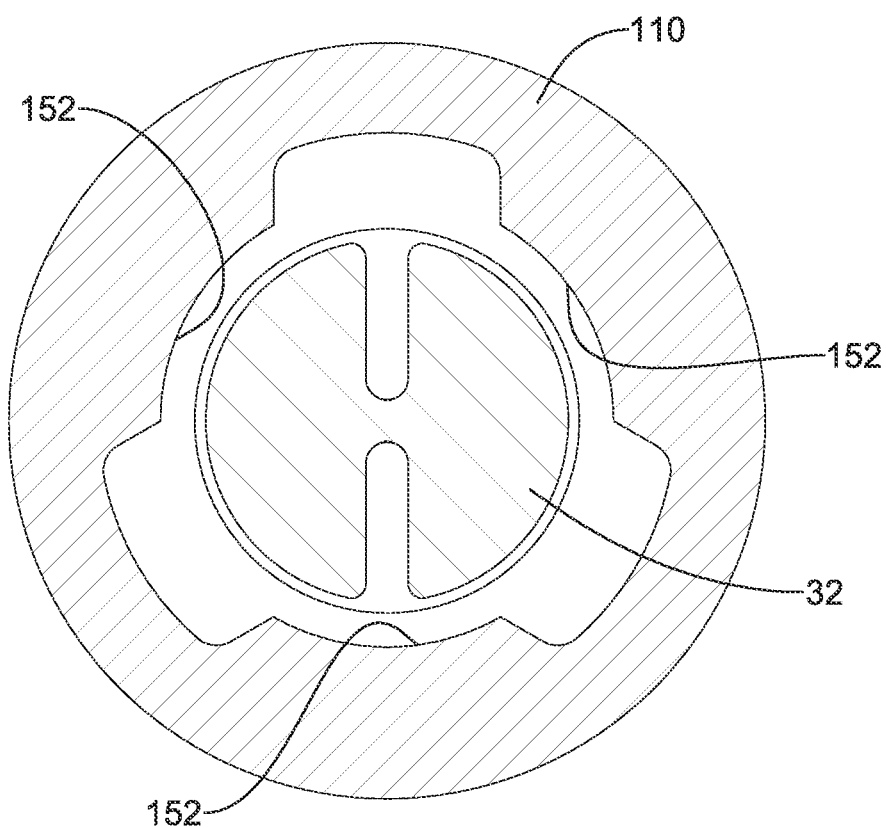
FIG. 5C is a cross-sectional view taken along line 5C-5C of FIG. 5A.
Figure 5D:
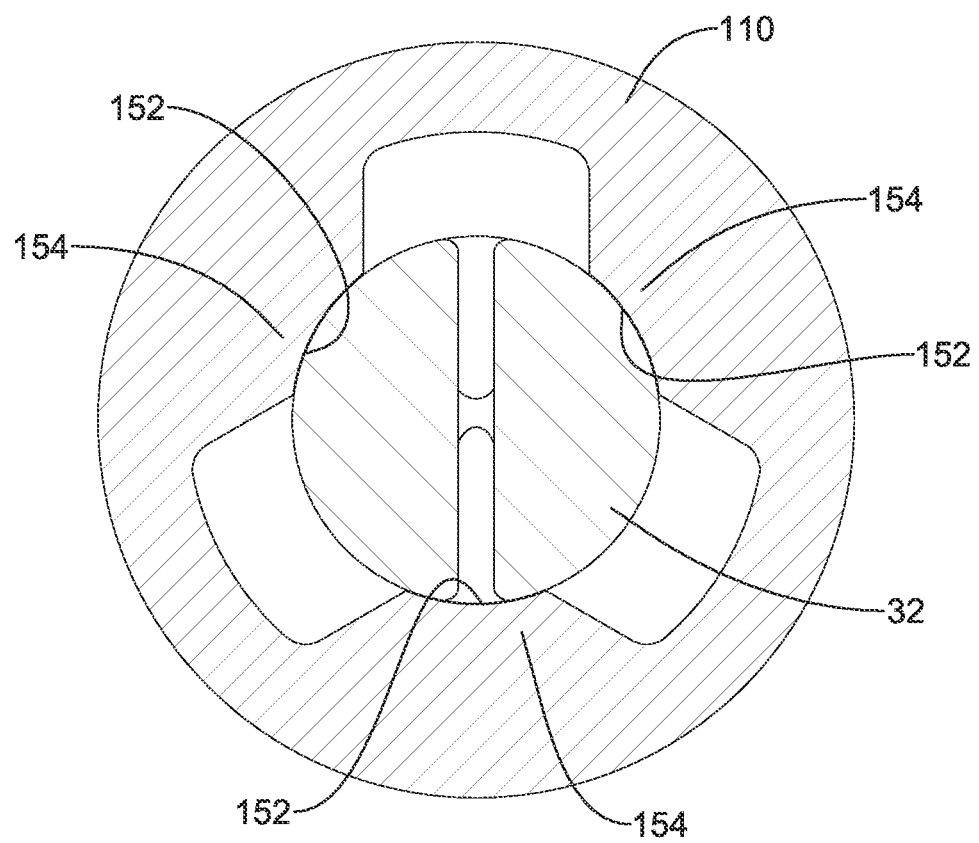
FIG. 5D is a cross-sectional view taken along line 5D-5D of FIG. 5B.

The implantable device 10 may be drawn into the chamber 130 with the snare 120 until the head portion 32 of the docking member 30 is positioned in a distal portion of the central opening 158 defined by the tapered surface 152, as shown in FIG. 5A. FIG. 5C, illustrates a transverse cross-section at this position, showing that the outer diameter of the head portion 32 may be less than the inner diameter of the tapered surface 152 at this position. The docking member 30 may then be drawn further proximally with the snare 120 to a more proximal location within the central opening 158 by applying a sufficient amount of force to the snare 120 to pull the head portion 32 into engagement with the tapered surface 152 a sufficient amount, as shown in FIG. 5B, forming an interference or frictional fit between the head portion 32 of the docking member 30 and the tapered surface 152 to lock the implantable device 10 within the chamber 130. FIG. 5D illustrates a transverse cross-section at this position, showing the head portion 32 in frictional engagement with the tapered surface 152. Unless a threshold amount of force is applied to the implantable device 10 to overcome the static frictional force between the head portion 32 and the tapered surface 152, the interference or frictional fit will retain the implantable device 10 within the chamber 130. The implantable device 10, retained in the chamber 130 with the retention feature 150 and/or the snare 120 may then be withdrawn from the heart H with the retrieval device 100.

Figure 6:
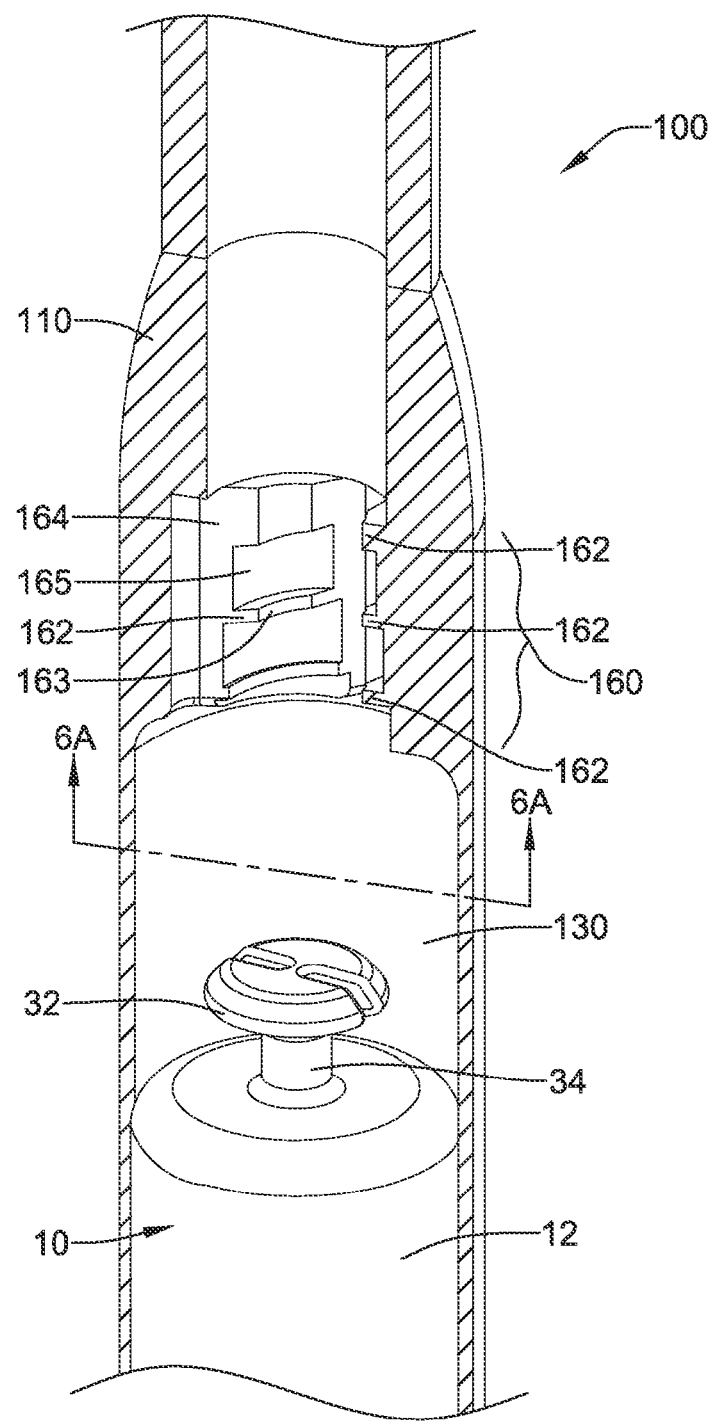
FIG. 6 is a perspective cross-sectional view of another exemplary retention feature of a retrieval device and a perspective view of an associated docking member of an implantable device.

Another exemplary embodiment of a retention feature 160 located within the retrieval catheter 110 is illustrated in FIG. 6. The retention feature 160 may be located within the retrieval catheter 110 proximal of a distal portion of the lumen of the retrieval catheter 110 defining a chamber 130 sized to receive the implantable device 10 therein.

The retention feature 160 shown in FIG. 6 may include internal threading 162 configured to threadably engage with the head portion 32 of the docking member 30. For example, the head portion 32 of the docking member 30 may be positionable between adjacent windings of the internal threading 162. In other instances, the head portion 32 of the docking member 30 may include external threading configured to threadably engage the internal threading 162 of the retention feature 160.

Figure 6A:
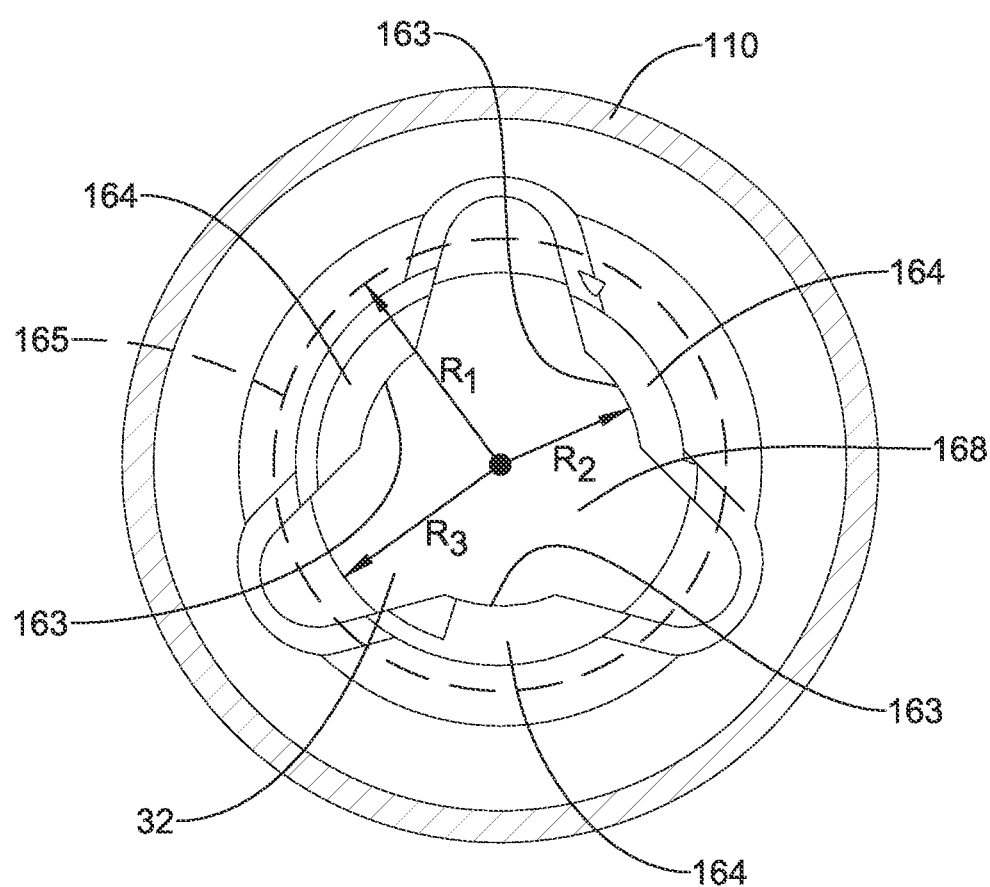
FIG. 6A is a cross-sectional view taken along line 6A-6A of FIG. 6.

As shown in FIG. 6A, a root 165 of the internal threading 162 may have a major diameter ($2R_1$) greater than an outer diameter ($2R_3$) of the head portion 32 of the docking member 30 while a crest 163 of the internal threading 162 may have a minor diameter ($2R_2$) less than the outer diameter ($2R_3$) of the head portion 32 of the docking member 30.

Accordingly, as the head portion 32 is threadably engaged with the internal threading 162 through rotational motion of the retention feature 160 (e.g., rotational motion of the retrieval catheter 110) relative to the implantable device 10, the implantable device 10 may be prevented from being expelled from the chamber 130 while withdrawing the implantable device 10 from the patient with the retrieval device 100.

In some instances, the internal threading 162 may be continuous through one or more, or a plurality of revolutions. In other instances, the internal threading 162 may be discontinuous. For example, as shown in FIGS. 6 and 6A, in some instances the retention feature 160 may include one or more, or a plurality of lands 164 extending radially inward from an inner surface of the retrieval catheter 110. The lands 164 may be symmetrically or asymmetrically spaced apart around the inner surface. In some instances, as shown in FIG. 6A, internal threading 162 may include a plurality of discontinuous threaded segments, with one or more of the discontinuous segments being associated with each of the lands 164. In other instances, the internal threading 162, which may be continuous or discontinuous, may extend directly from the inner surface of the retrieval catheter 110.

In some instances, the internal threading 162 and/or the lands 164 may be formed as a unitary structure with the portion of the retrieval catheter 110 defining the chamber 130, or other component of the retrieval catheter 110. However, in other instances, the internal threading 162 and/or the lands 164 may be formed as a separate structure.

Figure 7A:
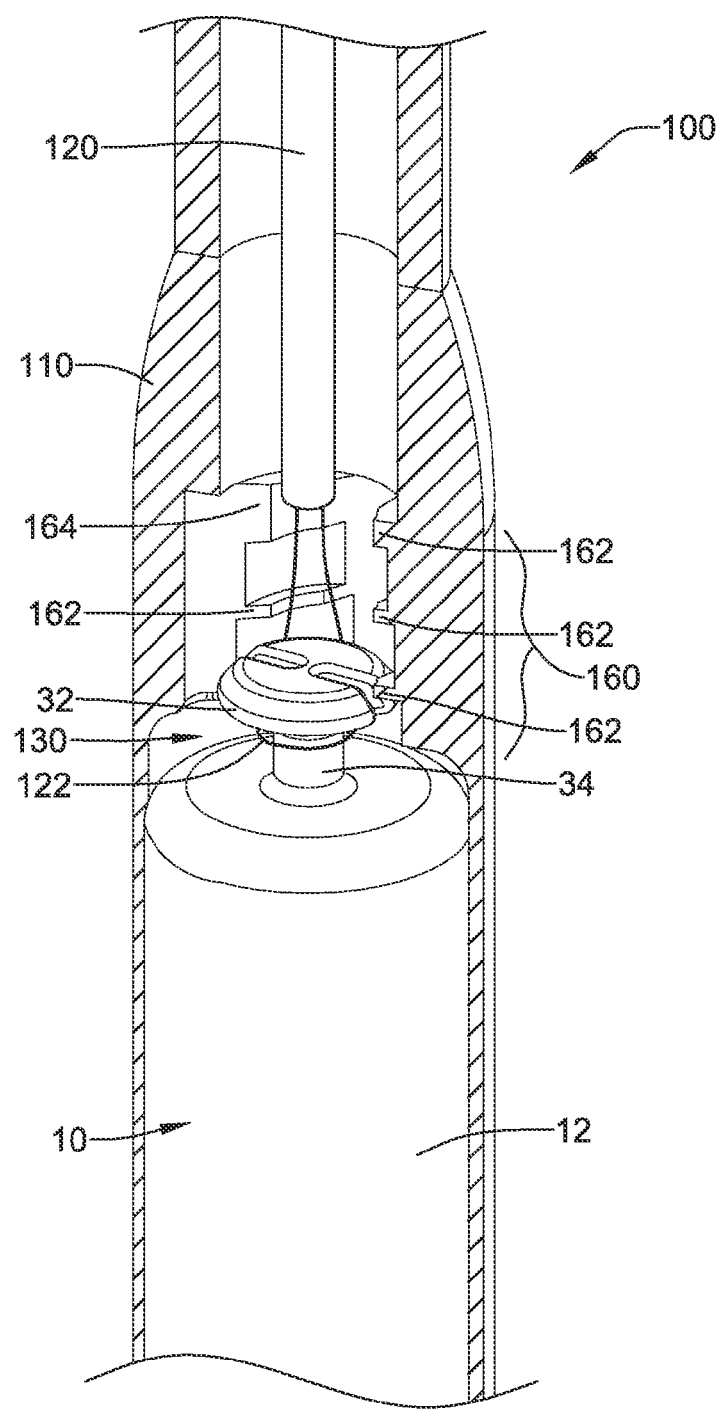
FIGS. 7A and 7B are cross-sectional views illustrating retention of the docking member with the retention feature of FIG. 6 during a retrieval procedure.
Figure 7B:
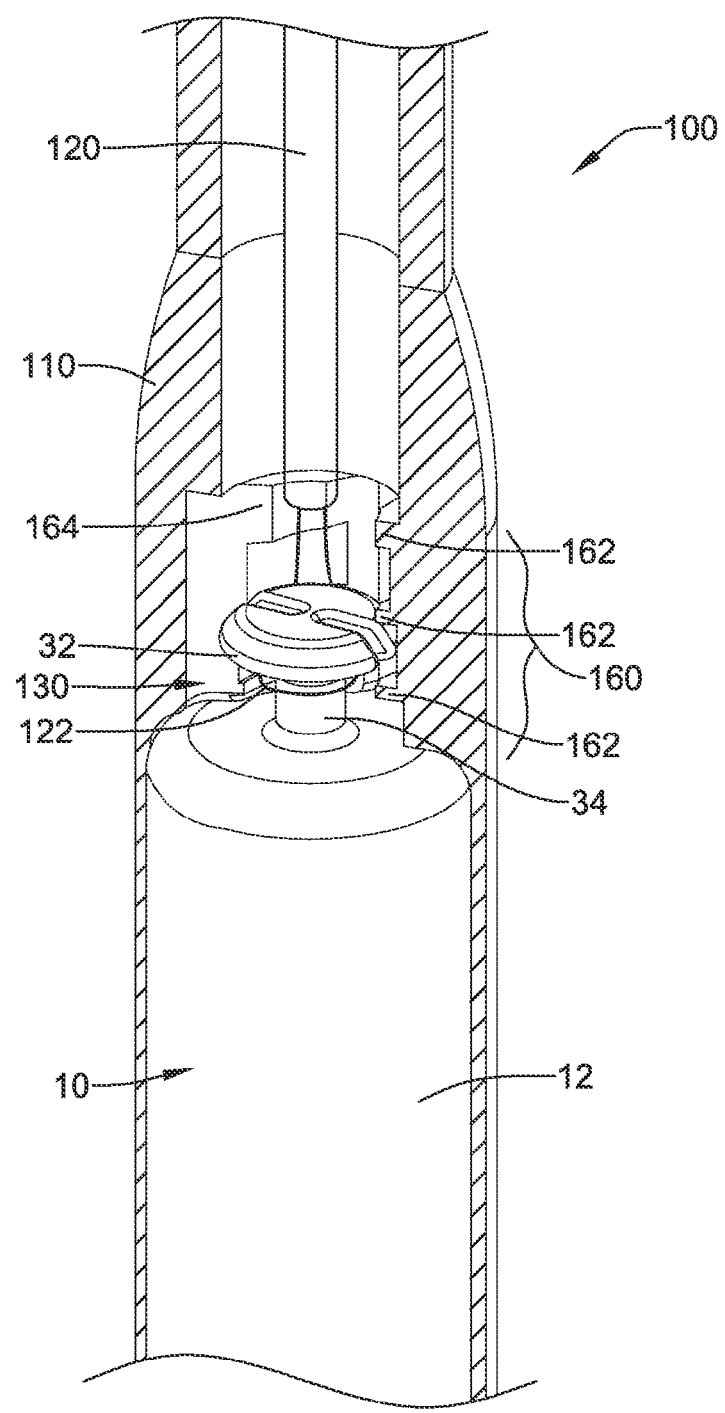

FIGS. 7A and 7B illustrate an exemplary process of engaging the implantable device 10 with the retention feature 160 during a retrieval procedure. During the retrieval procedure the implantable device 10 may be pulled into the chamber 130 of the retrieval catheter 110, such as with the snare 120. For example, with the loop 122 cinched around the docking member 30, the snare 120 may be actuated proximally relative to the retrieval catheter 110 to draw the housing 12 of the implantable device 10 into the chamber 130 at the distal end of the retrieval catheter 110.

The implantable device 10 may be drawn into the chamber 130 with the snare 120 until the docking member 30 is just distal of the internal threading 162, as shown in FIG. 7A. The retention structure 160, may then be rotated relative to the implantable device 10, such as by rotating the retrieval catheter 110, or a drive shaft thereof, to threadably engage the head portion 32 of the docking member 30 with the internal threading 162 as the head portion 32 moves into the central opening 168 of the retention feature 160, as shown in FIG. 7B, forming a threaded connection between the head portion 32 of the docking member 30 and the internal threading 162 to lock the implantable device 10 within the chamber 130. Unless a sufficient counter rotational movement between the implantable device and the internal threading 162 is applied to unscrew the docking member 30 from the internal threading 162, the threaded engagement with the internal threading 162 will retain the implantable device 10 within the chamber 130. The implantable device 10, retained in the chamber 130 with the retention feature 160 and/or the snare 120 may then be withdrawn from the heart H with the retrieval device 100.

Figure 8:
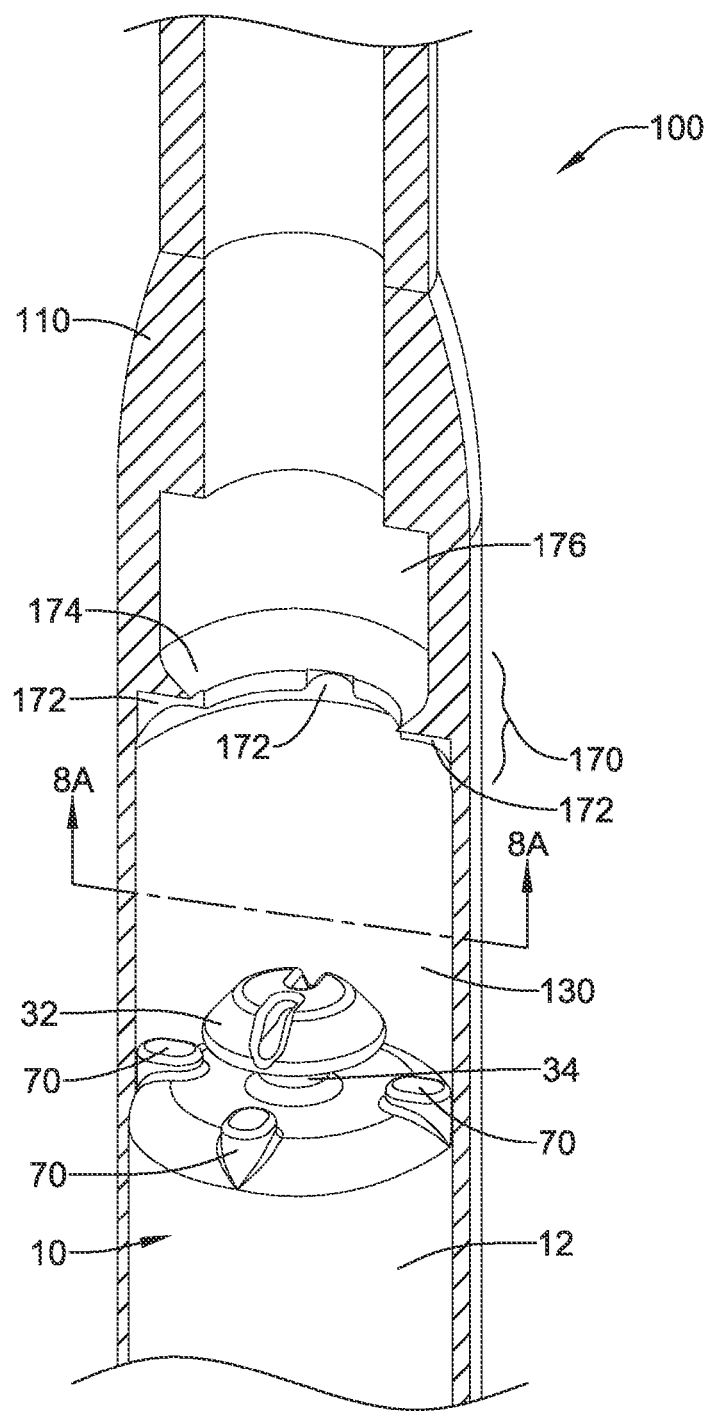
FIG. 8 is a perspective cross-sectional view of another exemplary retention feature of a retrieval device and a perspective view of an associated docking member of an implantable device.

Another exemplary embodiment of a retention feature 170 located within the retrieval catheter 110 is illustrated in FIG. 8. The retention feature 170 may be located within the retrieval catheter 110 proximal of a distal portion of the lumen of the retrieval catheter 110 defining a chamber 130 sized to receive the implantable device 10 therein.

Figure 8A:
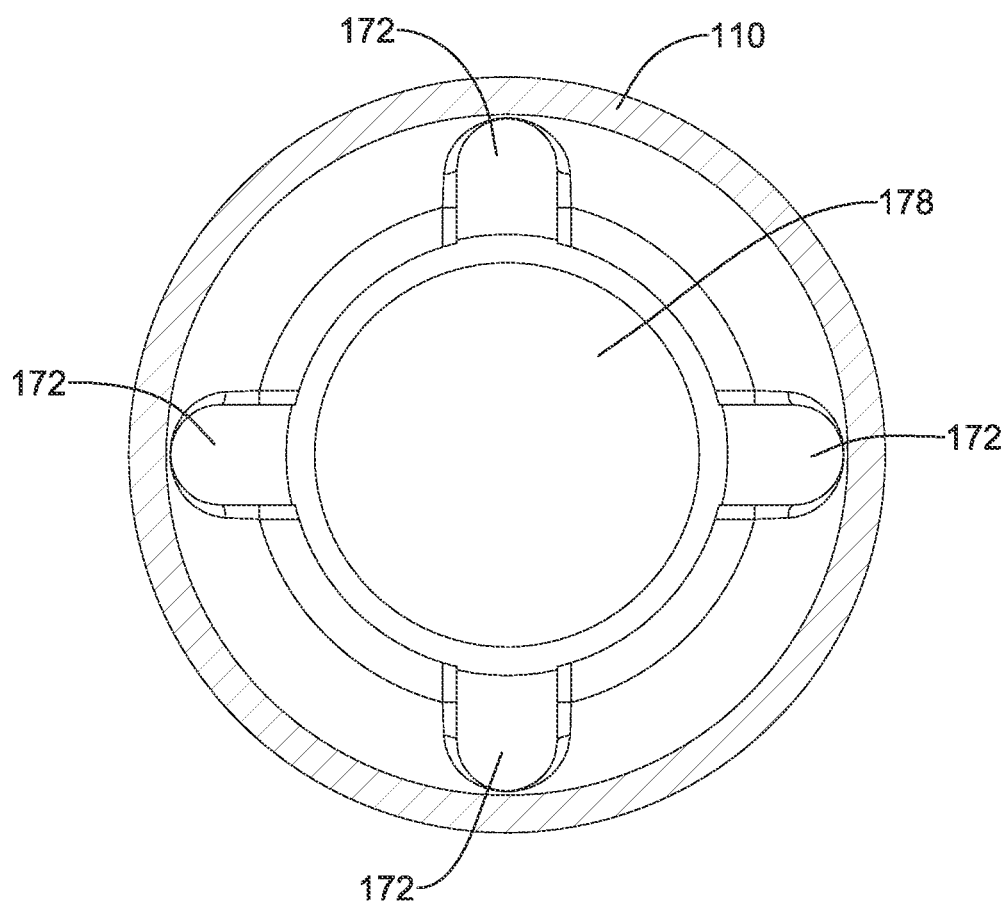
FIG. 8A is a cross-sectional view taken along line 8A-8A of FIG. 8.

The retention feature 170 shown in FIG. 8 may include a circumferential rim 174 extending radially inward from an interior surface of the retention feature 170 and/or the chamber 130. A central opening 178 defined by the circumferential rim 174 may be sized to permit the head portion 32 of the docking member 30 to pass proximally therethrough. The retention feature 170 may include one or more, or a plurality of recesses 172 symmetrically or asymmetrically arranged around the circumferential rim 174 and opening distally to the chamber 130. For example, in the illustrated embodiment as shown in FIG. 8A, the retention feature 170 may include four recesses 172 symmetrically arranged around the circumferential rim 174. However, in other instances, the retention feature 170 may include a different number of recesses 172, if desired.

The implantable device 10 may include one or more, or a plurality of protuberances 70 configured to be positionable in the recess(es) 172 to form a press fit therewith. For example, in the illustrated embodiment, the implantable device 10 may include four protuberances 70 symmetrically arranged around the proximal end of the housing 12 and extending proximally therefrom. However, in other instances, the protuberances 70 may be arranged in a different manner, if desired.

In some instances, the circumferential rim 174 may be formed as a unitary structure with the portion of the retrieval catheter 110 defining the chamber 130, or other component of the retrieval catheter 110. However, in other instances, the circumferential rim 174 may be formed as a separate structure.

Figure 9A:
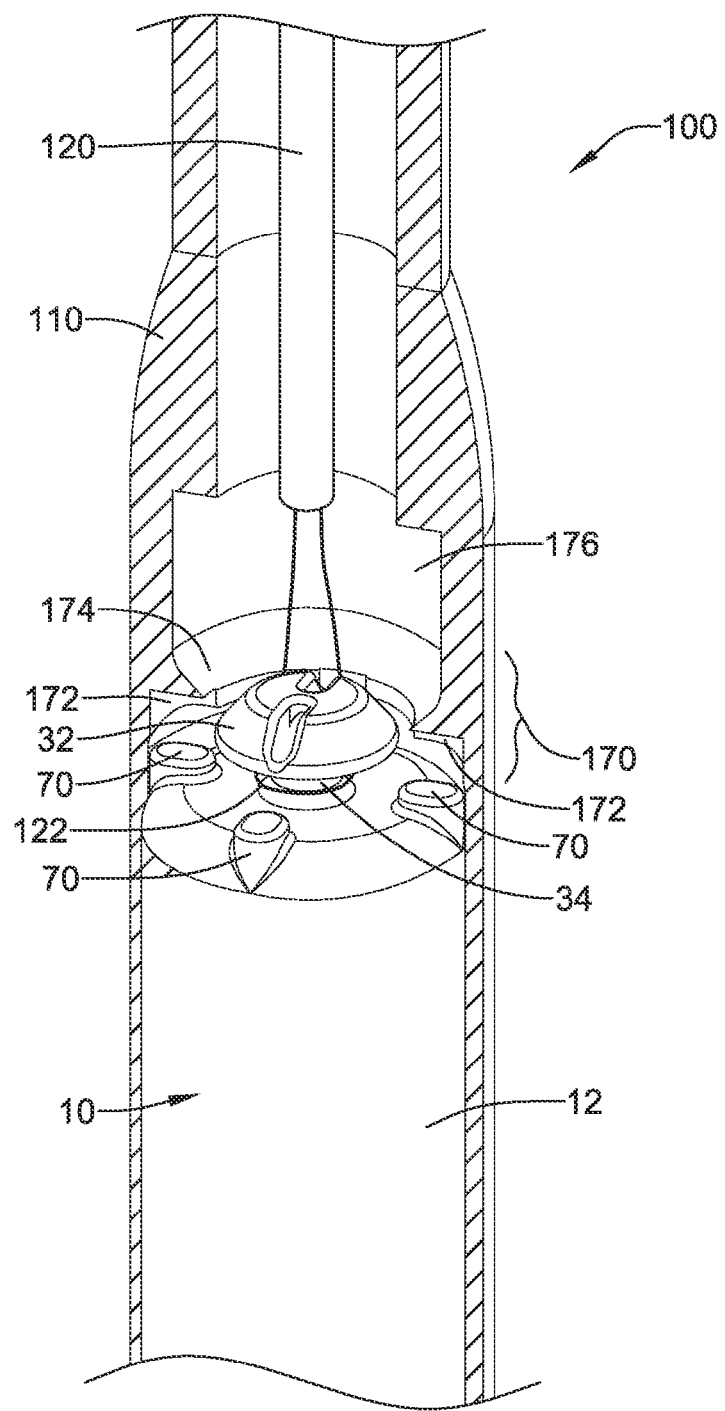
FIGS. 9A and 9B are cross-sectional views illustrating retention of the docking member with the retention feature of FIG. 8 during a retrieval procedure.
Figure 9B:
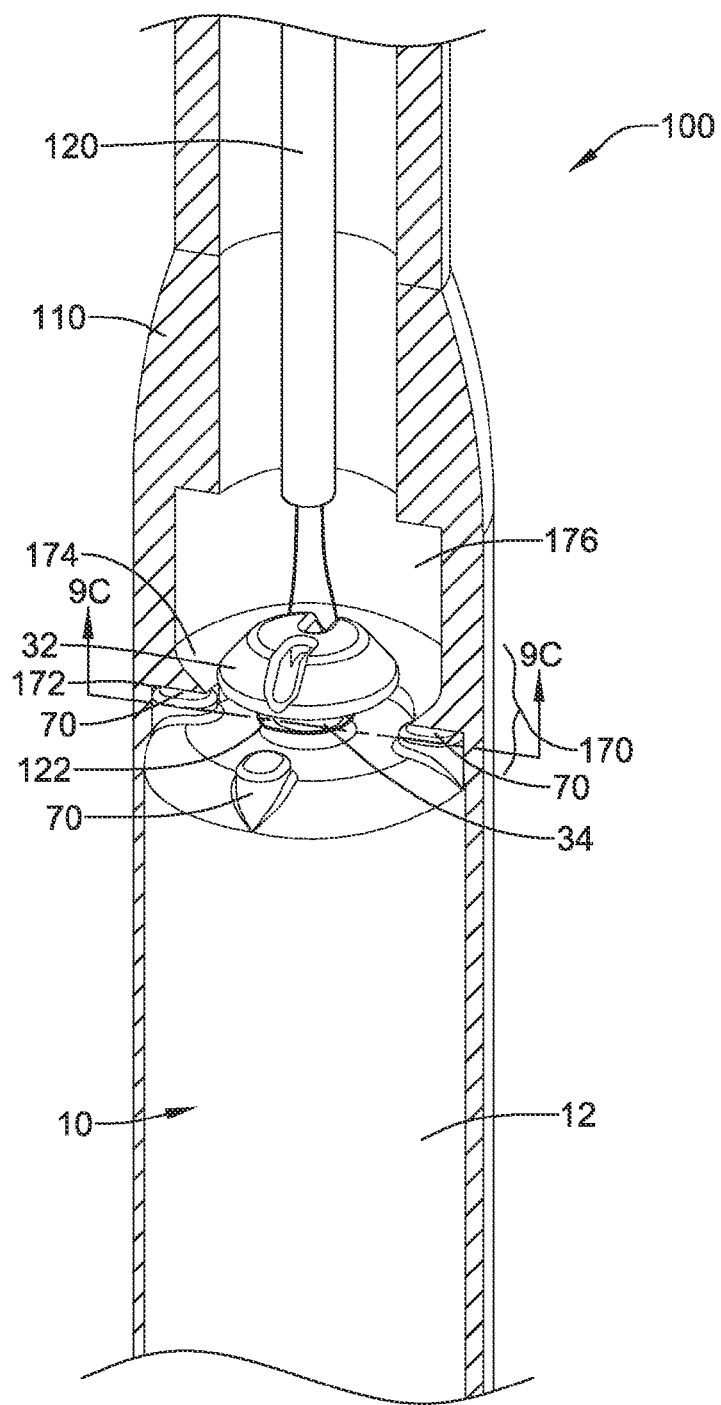

FIGS. 9A and 9B illustrate an exemplary process of engaging the implantable device 10 with the retention feature 170 during a retrieval procedure. During the retrieval procedure the implantable device 10 may be pulled into the chamber 130 of the retrieval catheter 110, such as with the snare 120. For example, with the loop 122 cinched around the docking member 30, the snare 120 may be actuated proximally relative to the retrieval catheter 110 to draw the housing 12 of the implantable device 10 into the chamber 130 at the distal end of the retrieval catheter 110.

Figure 9C:
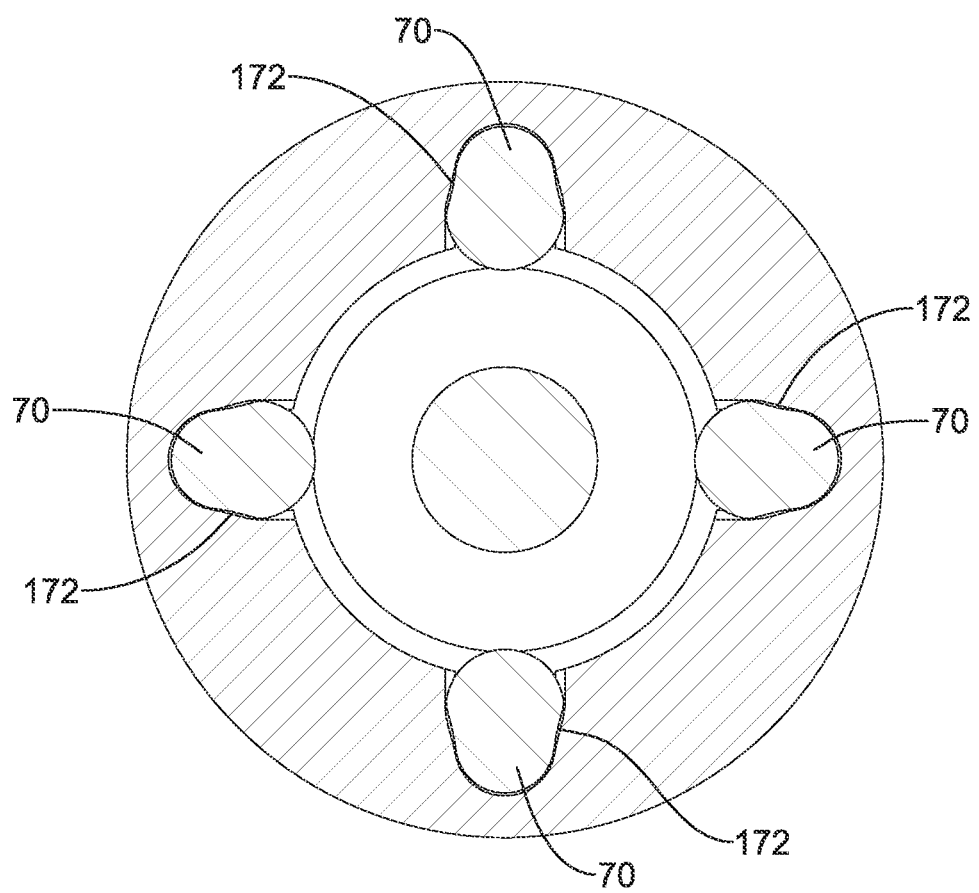
FIG. 9C is a cross-sectional view taken along line 9C-9C of FIG. 9B.

The implantable device 10 may be drawn into the chamber 130 with the snare 120 until the protuberances 70 are located just distal of the recesses 172, as shown in FIG. 9A. In some instances, the retention feature 170 (e.g., the retrieval catheter 110, or a portion thereof) may need to be rotated relative to the implantable device 10 to align the recesses 172 with the protuberances 70, if the recesses 172 are not already aligned with the protuberances 70. The docking member 30 may then be drawn further proximally with the snare 120 into the central opening 178 by applying a sufficient amount of force to the snare 120 to pull the protuberances 70 into engagement with the recesses 172 a sufficient amount, as shown in FIG. 9B, forming an interference or frictional fit between the protuberances 70 and the recesses 172 to lock the implantable device 10 within the chamber 130. FIG. 9C illustrates a transverse cross-section at this position, showing the protuberances 70 pressed into and in frictional engagement with the recesses 172. Unless a threshold amount of force is applied to the implantable device 10 to overcome the static frictional force between the protuberances 70 and the recesses 172, the interference or frictional fit will retain the implantable device 10 within the chamber 130. The implantable device 10, retained in the chamber 130 with the retention feature 170 and/or the snare 120 may then be withdrawn from the heart H with the retrieval device 100.

Figure 10:
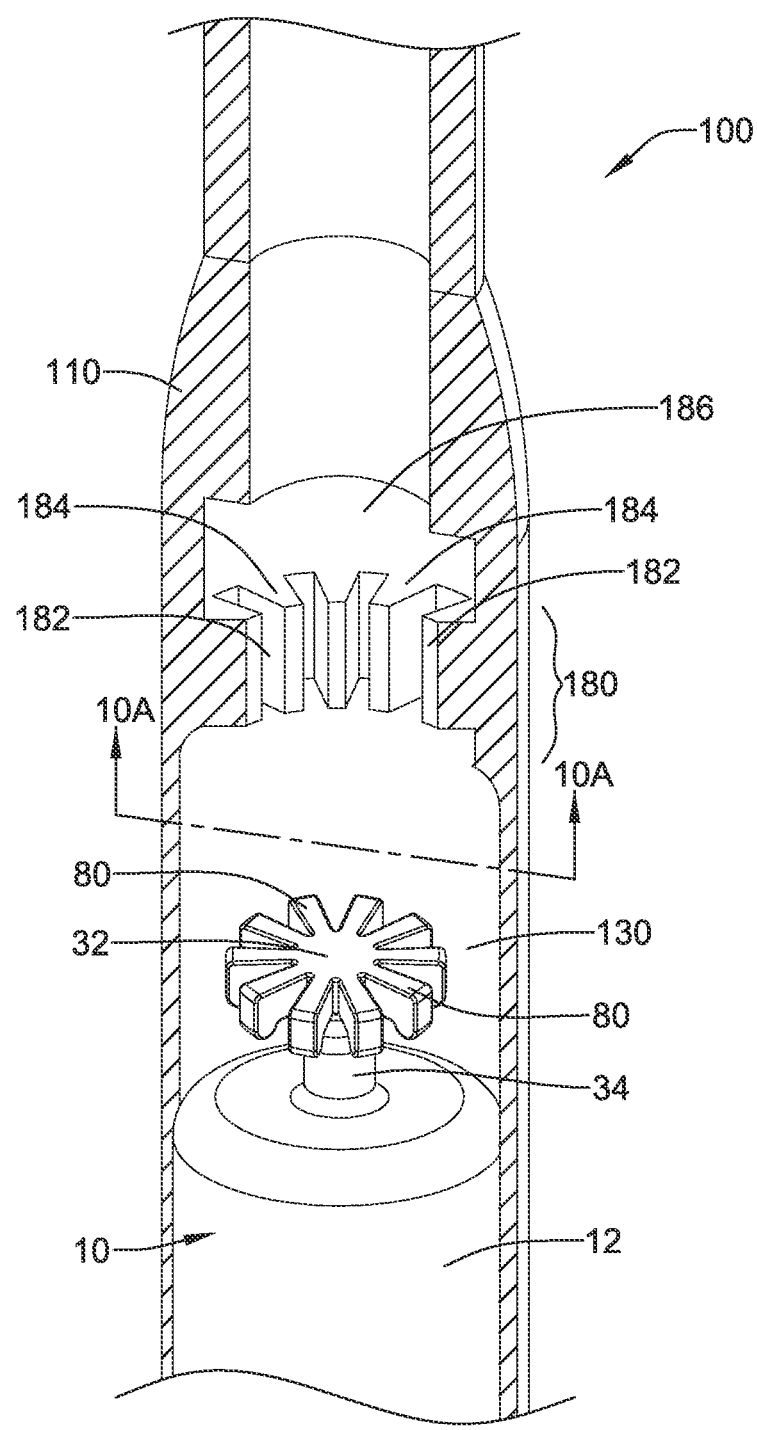
FIG. 10 is a perspective cross-sectional view of another exemplary retention feature of a retrieval device and a perspective view of an associated docking member of an implantable device.

Another exemplary embodiment of a retention feature 180 located within the retrieval catheter 110 is illustrated in FIG. 10. The retention feature 180 may be located within the retrieval catheter 110 proximal of a distal portion of the lumen of the retrieval catheter 110 defining a chamber 130 sized to receive the implantable device 10 therein.

The retention feature 180 shown in FIG. 10 may include a plurality of ribs 184 extending radially inward from an interior surface of the retention feature 180 and/or the chamber 130. A central opening 188 radially inward of the plurality of ribs 184 may be sized to permit the head portion 32 of the docking member 30 to pass proximally therein to permit engagement of the ribs 184 with the head portion 32 of the docking member 30.

Figure 10A:
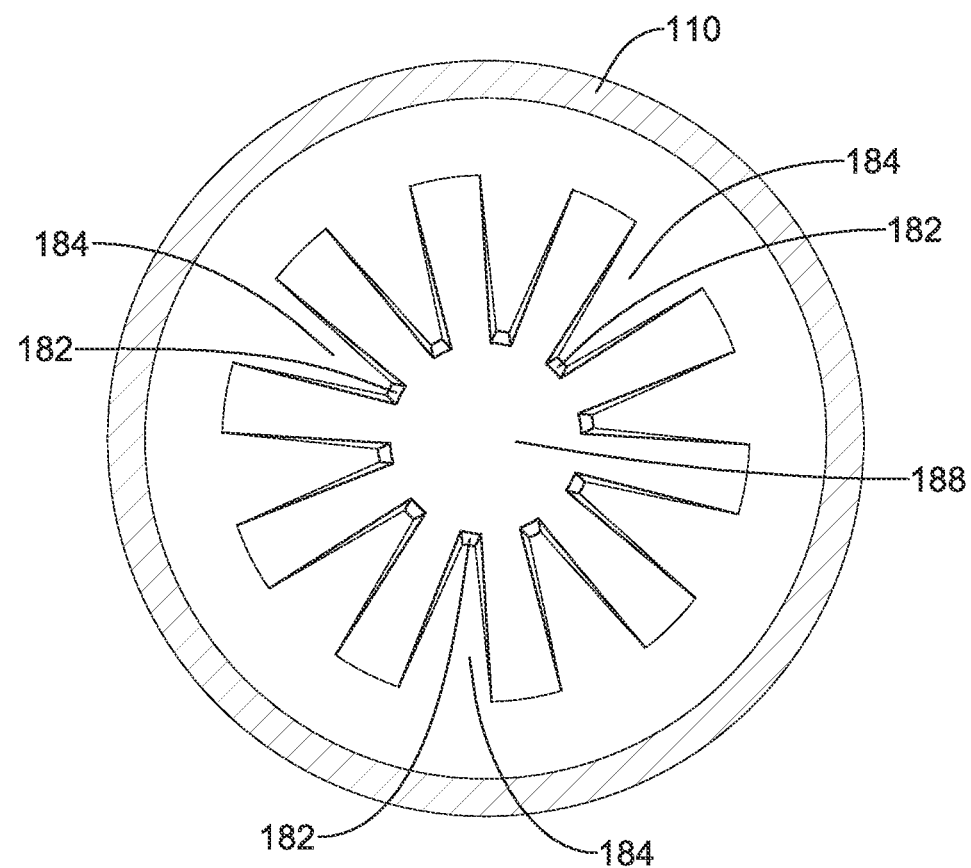
FIG. 10A is a cross-sectional view taken along line 10A-10A of FIG. 10.

The ribs 184 may be symmetrically or asymmetrically arranged around the interior surface 186. For example, in the illustrated embodiment as shown in FIG. 10A, the retention feature 180 may include ten ribs 184 symmetrically arranged around the central opening 188. However, in other instances, the retention feature 180 may include a different number of ribs 184, if desired.

The ribs 184 may include surfaces 182, such as tapered surfaces 182. For example, the ribs 184 may include a radially inward surface 182 and opposing side surfaces 182. In some instances, the radially inward surface 182 of the ribs 184 may taper proximally from a first diameter to a second diameter less than the first diameter and/or the side surfaces 182 of a rib 184 may taper toward one another in a distal direction.

The head portion 32 of the docking member 30 of the implantable device 10 may include one or more, or a plurality of radially projecting spokes 80 configured to be positionable between the ribs 184 to form a press fit against one or more of the surfaces 182 of the ribs 184. In some instances, the ribs 184 may be deformable, such that as the spokes 80 are drawn between the ribs 184 and pressed there against, the ribs 184 may be deformed.

In the illustrated embodiment, the implantable device 10 may include ten radially extending spokes 80 symmetrically arranged around the head portion 32 of the docking member 30. However, in other instances, the spokes 80 may be arranged in a different manner, if desired. The surfaces 182 of the ribs 184 may be configured to be pressed against a surface of the radially projecting spokes 80.

Figure 11:
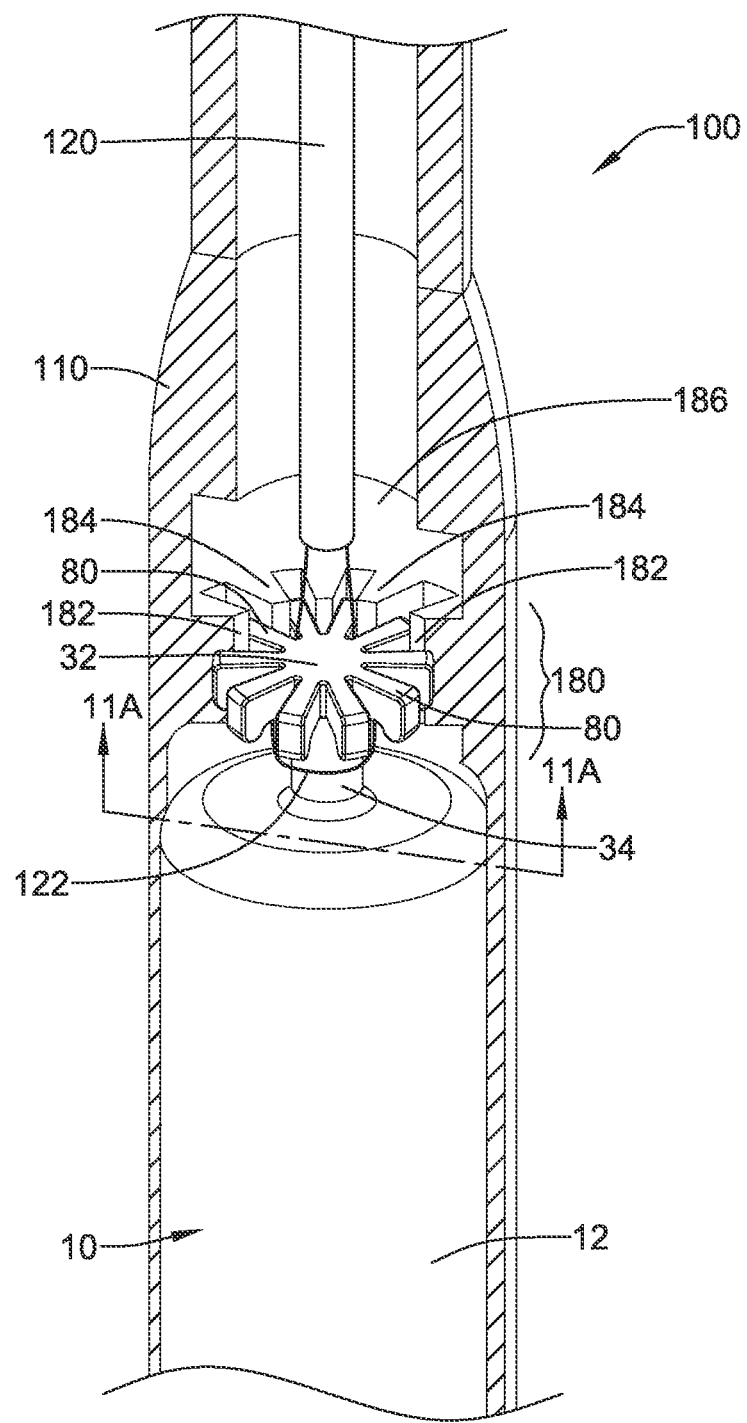
FIG. 11 is a cross-sectional view illustrating retention of the docking member with the retention feature of FIG. 10 during a retrieval procedure.

FIG. 11 illustrates an exemplary process of engaging the implantable device 10 with the retention feature 180 during a retrieval procedure. During the retrieval procedure the implantable device 10 may be pulled into the chamber 130 of the retrieval catheter 110, such as with the snare 120. For example, with the loop 122 cinched around the docking member 30, the snare 120 may be actuated proximally relative to the retrieval catheter 110 to draw the housing 12 of the implantable device 10 into the chamber 130 at the distal end of the retrieval catheter 110.

Figure 11A:
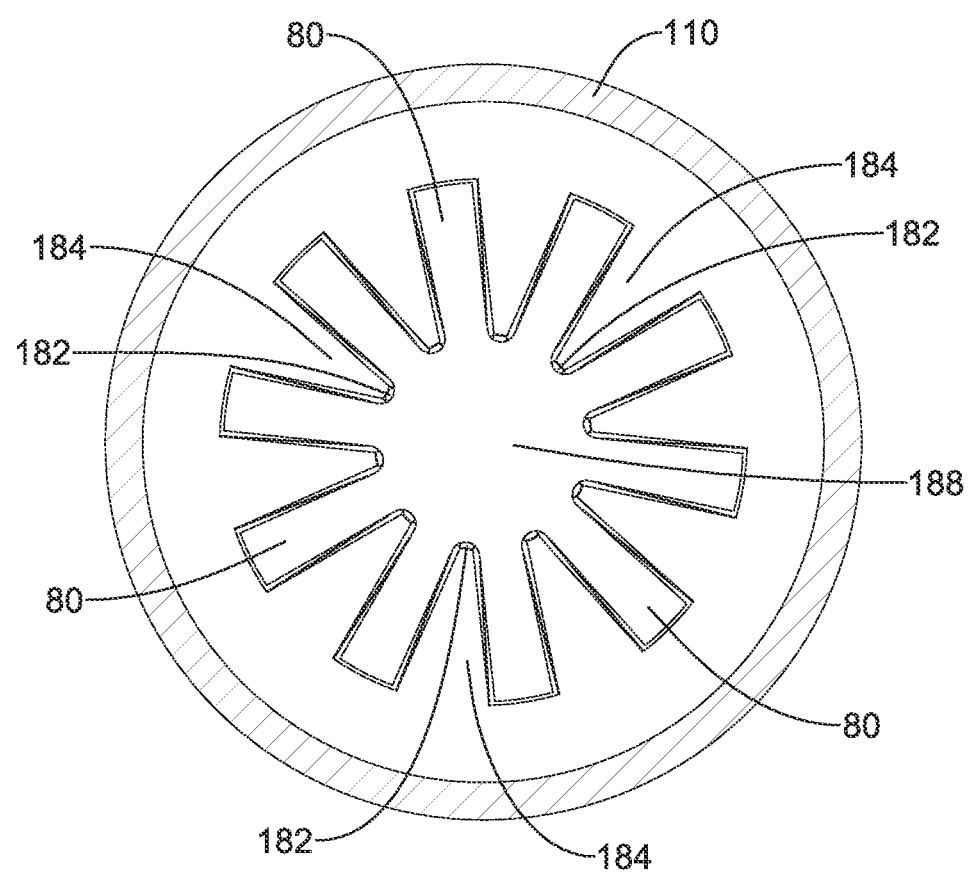
FIG. 11A is a cross-sectional view taken along line 11A-11A of FIG. 11.

The implantable device 10 may be drawn into the chamber 130 with the snare 120 until the spokes 80 are positioned between the ribs 184. In some instances, the retention feature 180 (e.g., the retrieval catheter 110, or a portion thereof) may need to be rotated relative to the implantable device 10 to align the ribs 184 with the space between the spokes 80, if the ribs 184 are not already aligned with the spaces between the spokes 80. The docking member 30 may then be drawn further proximally with the snare 120 into the central opening 188 by applying a sufficient amount of force to the snare 120 to pull the spokes 80 into engagement with the ribs 184 a sufficient amount, as shown in FIG. 11, forming an interference or frictional fit between the spokes 80 and the ribs 184 to lock the implantable device 10 within the chamber 130. Thus, the ribs 184 may be intermeshed with the spokes 80 of the docking member 30. FIG. 11A illustrates a transverse cross-section at this position, showing the spokes 80 pressed against and in frictional engagement with the ribs 184. Unless a threshold amount of force is applied to the implantable device 10 to overcome the static frictional force between the spokes 80 and the ribs 184, the interference or frictional fit will retain the implantable device 10 within the chamber 130. The implantable device 10, retained in the chamber 130 with the retention feature 180 and/or the snare 120 may then be withdrawn from the heart H with the retrieval device 100.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An assembly for retrieving an implantable cardiac pacing device, comprising:
   an implantable cardiac pacing device having a housing, an electrode positioned proximate a distal end of the housing, and a docking member extending from a proximal end of the housing opposite the distal end, the docking member including a head portion and a neck portion extending between the housing and the head portion; and
   a retrieval device including:
      a retrieval catheter having a proximal end, a distal end, and a lumen extending into the retrieval catheter from the distal end;
      a snare advanceable from the distal end of the retrieval catheter, the snare having a loop configured to be coupled to the docking member to draw the implantable cardiac pacing device into the lumen of the retrieval catheter;
   wherein the retrieval catheter includes a retention feature arranged on an inner wall of the retrieval catheter and extending into the lumen configured to engage the head portion of the docking member to facilitate retention of the implantable cardiac pacing device in the lumen after drawing the implantable cardiac pacing device into the lumen of the retrieval catheter with the snare, wherein the retention feature includes a tapered surface configured to form an interference fit with the head portion of the docking member, wherein the tapered surface has a length, the length of the tapered surface facing a central longitudinal axis of the retrieval catheter both prior to and after the tapered surface contacts the head portion of the docking member, the tapered surface extending in a longitudinal direction from a first distal diameter greater than an outer diameter of the head portion of the docking member to a second proximal diameter less than the outer diameter of the head portion of the docking member.

2. The assembly of claim 1, wherein the tapered surface is a discontinuous frustoconical surface.

3. The assembly of claim 1, wherein a distal portion of the lumen distal of the retention feature is sized to receive the housing of the implantable cardiac pacing device therein.

4. The assembly of claim 1, wherein the snare extends through a central opening through the retention feature.

5. An assembly for retrieving an implantable cardiac pacing device, comprising:
   an implantable cardiac pacing device having a housing, an electrode positioned proximate a distal end of the housing, and a docking member extending from a proximal end of the housing opposite the distal end, the docking member including a head portion and a neck portion extending between the housing and the head portion; and
   a retrieval device including:
      a retrieval catheter having a proximal end, a distal end, and a lumen extending into the retrieval catheter from the distal end;
      a snare advanceable from the distal end of the retrieval catheter, the snare having a loop configured to be coupled to the docking member to draw the implantable cardiac pacing device into the lumen of the retrieval catheter;
   wherein the retrieval catheter includes a retention feature in the lumen configured to engage the head portion of the docking member to facilitate retention of the implantable cardiac pacing device in the lumen after drawing the implantable cardiac pacing device into the lumen of the retrieval catheter with the snare, wherein the retention feature includes internal threading configured to threadably engage the head portion of the docking member.

6. The assembly of claim 5, wherein the head portion of the docking member is positionable between adjacent windings of the internal threading.

7. The assembly of claim 5, wherein a minor diameter of the internal threading is less than an outer diameter of the head portion of the docking member and a major diameter of the internal threading is greater than the outer diameter of the head portion of the docking member.

8. The assembly of claim 5, wherein the internal threading is discontinuous.

9. An assembly for retrieving an implantable cardiac pacing device, comprising:
   an implantable cardiac pacing device having a housing, an electrode positioned proximate a distal end of the housing, and a docking member extending from a proximal end of the housing opposite the distal end, the docking member including a head portion and a neck portion extending between the housing and the head portion; and
   a retrieval device including:
      a retrieval catheter having a proximal end, a distal end, and a lumen extending into the retrieval catheter from the distal end;
      a snare advanceable from the distal end of the retrieval catheter, the snare having a loop configured to be coupled to the docking member to draw the implantable cardiac pacing device into the lumen of the retrieval catheter;

wherein the retrieval catheter includes a retention feature arranged on an inner wall of the retrieval catheter and extending into the lumen configured to engage the head portion of the docking member to facilitate retention of the implantable cardiac pacing device in the lumen after drawing the implantable cardiac pacing device into the lumen of the retrieval catheter with the snare, wherein the retention feature includes a plurality of spaced apart recesses for receiving a plurality of spaced apart protuberances extending from the implantable cardiac pacing device, wherein the retention feature includes a circumferential rim projecting into the lumen, wherein the plurality of spaced apart recesses are arranged around the circumferential rim, and wherein the plurality of spaced apart protuberances extend radially away from a central longitudinal axis of the cardiac pacing device.

10. The assembly of claim 9, wherein the plurality of protuberances are press fit into the a plurality of recesses.

11. The assembly of claim 9, wherein the retention feature includes a plurality of radially extending ribs separated by the plurality of spaced apart recesses, wherein the plurality of protuberances include a plurality of radially extending spokes on the head portion of the docking member configured to intermesh with the plurality of radially extending ribs.

12. The assembly of claim 11, wherein each of the ribs is configured to be pressed between adjacent spokes of the head portion of the docking member.

13. The assembly of claim 9, wherein the plurality of spaced apart protuberances are disposed on the housing of the implantable cardiac pacing device.

14. The assembly of claim 13, wherein the plurality of spaced apart protuberances extend proximally from the proximal end of the housing of the implantable cardiac pacing device.

* * * * *